United States Patent [19]

Enomoto et al.

[11] 4,277,633

[45] Jul. 7, 1981

[54] PALLADIUM COMPLEX, PROCESS FOR THE PREPARATION THEREOF AND CATALYST FOR PRODUCING 1,3-DIENE OLIGOMERS

[75] Inventors: Satoru Enomoto, Fujisawa; Hisayuki Wada, Tokyo; Sadao Nishita, Tokyo; Yutaka Mukaida, Tokyo; Mikiro Yanaka, Matsudo; Hitoshi Takita, Tokyo, all of Japan

[73] Assignee: Kureha Kagaku Kogyo Kabushiki Kaisha, Tokyo, Japan

[21] Appl. No.: 57,030

[22] Filed: Jul. 12, 1979

Related U.S. Application Data

[62] Division of Ser. No. 904,407, May 10, 1978, Pat. No. 4,196,135.

[30] Foreign Application Priority Data

May 18, 1977 [JP] Japan .................................. 52-56311

[51] Int. Cl.$^3$ ............................................. C07C 33/02
[52] U.S. Cl. ................................... 568/879; 568/690; 568/878; 568/813; 260/345.1; 560/238; 560/241
[58] Field of Search ................ 560/238, 241; 568/878, 568/879, 690; 585/509, 514, 527; 260/345.1

[56] References Cited

U.S. PATENT DOCUMENTS

| | | | |
|---|---|---|---|
| 3,530,187 | 9/1970 | Shryne | 568/680 |
| 3,576,011 | 4/1971 | Haynes | 260/345.1 |
| 3,670,032 | 6/1972 | Romanelli | 585/509 |
| 3,720,697 | 3/1973 | Fenton | 260/429 R |
| 3,798,278 | 3/1974 | Jung | 568/878 |
| 3,825,545 | 7/1974 | Fenton | 260/429 R |
| 3,891,684 | 6/1975 | Jung | 260/492 R |
| 3,992,456 | 11/1976 | Atkins et al. | 585/509 |

FOREIGN PATENT DOCUMENTS

47-20204  6/1972  Japan ..................................... 568/690

OTHER PUBLICATIONS

Manyek et al., Tetrahedron letters, No. 43, pp. 3813–3816, 1970.
Chemical Abstracts 79105234p, (1973).

*Primary Examiner*—Howard T. Mars
*Attorney, Agent, or Firm*—Wegner & Bretschneider

[57] ABSTRACT

The palladium complex disclosed herein is bis[tri(ortho-tolyl)phosphine] :palladium which is produced by reacting a palladium salt with tri(ortho-tolyl)phosphine and reducing the resultant bis[tri(ortho-tolyl)phosphine] palladium salt with an alcoholic alkali. This complex is useful as a catalyst for the production of 1,3-diene oligomers.

2 Claims, 2 Drawing Figures

PALLADIUM COMPLEX, PROCESS FOR THE PREPARATION THEREOF AND CATALYST FOR PRODUCING 1,3-DIENE OLIGOMERS

This is a division of application Ser. No. 904,407 filed May 10, 1978 now U.S. Pat. No. 4,196,135.

FIELD OF THE INVENTION

This invention relates to a novel complex, bis[tri(ortho-tolyl)phosphine] palladium, a process for the preparation thereof and a catalyst including such a complex and being usable for the production of 1,3-diene oligomers.

BACKGROUND OF THE INVENTION

Palladium has been long used as a reagent for organic syntheses. For example, the Wacker process capable of producing acetaldehyde from ethylene by using palladium chloride as a catalyst has been widely industrialized. On the other hand, the low-valent complexes of palladium are drawing attention of the industry for their availability as catalysts for organic syntheses such as dimerization of 1,3-dienes, and for this purpose, there are known a variety of zero-valent palladium complexes containing an organic phosphine as the ligand. These complexes have structures which differ in coordination number depending on the type of the ligand used, and naturally they differ from each other in physicochemical properties as well as in catalytic performance. However, the known zero-valence palladium phosphine complexes are unstable because they are low in heat resistance and also slowly decompose when left in the air. Although some types of such complexes have a relatively high decomposition temperature, they are vulnerable to oxidation in the air. Therefore, a keen need has developed in the industry for a zero-valent palladium complex which is stable in the air and yet high in heat resistance and is able to serve as an excellent catalyst for the organic syntheses.

There are known various methods for effecting dimerization of 1,3-dienes, including a method in which a combination of a divalent palladium salt and phosphine is used by reducing it to a lower state of valency in the reaction system and a method using a zero-valent palladium complex where an organic phosphine is incorporated as the ligand. The former method, however, is poor in efficiency as it is subject to restrictions in the reaction conditions such as dimerization temperature due to the essential requirement for reduction. Also, since there exist active materials of diverse valencies in the reaction system, the proportion of formation of the object reaction product (hereinafter referred to as selectivity) is low. As regards the latter method, although a variety of palladium complexes are known, each of them is a zero-valent palladium complex with a coordination number greater than 3. The complexes with a high coordination number are weak in activity and hence low in reaction rate in actual use. Thus, strong need has been felt for a catalyst which is further improved in selectivity, strong in activity even at low temperatures and high in reaction rate.

When a palladium-phosphine complex is used as a catalyst for an organic synthesis, the reaction generally proceeds in a homogeneous system. Therefore, this type of complex is very useful in performing the organic syntheses. However, because of the expensiveness of such complexes, it is highly desirable in the industrial processes to efficiently recover the complex after its use for putting the recovered complex to reuse. Since the palladium complex remains dissolved in the reaction solution, it has been generally practice to put the residual reaction solution to reuse or to recover metallic palladium by precipitating it from the residual solution. The former method, however, encounters the problem of an increasing amount of residual solution due to by-production of high-boiling matter in repeated use of the solution and also the problem of treatment of that portion of the catalyst which has lost its activity during the reaction. On the other hand, the latter method encounters the problem of a complicated operation for reactivating the recovered material, and also this method, although capable of recovering palladium, involves difficulties in recovery of organic phosphine.

SUMMARY OF THE INVENTION

The primary object of this invention, therefore, is to provide a novel palladium complex useful as catalyst for organic syntheses.

Another object of this invention is to provide a process for the preparation of such a palladium complex.

Still another important object of this invention is to provide a catalyst including the palladium complex and being usable for the production of oligomers of 1,3-dienes.

These and other objects and advantages of this invention will become apparent from the following detailed description of the invention.

As a result of extensive studies in search for palladium complexes useful as catalysts for organic syntheses, we found that a novel compound, bis[tri(ortho-tolyl)phosphine] palladium, composed of one atom of palladium and two molecules of tri(ortho-tolyl)phosphine is quite suited for use as a catalyst. The complex provided according to this invention is stable in air and also when used as a catalyst in dimerization of 1,3-diene, it shows high activity and reaction rate, excellent selectivity and is easy to recover after the reaction.

DETAILED DESCRIPTION OF THE INVENTION

Figure 1:
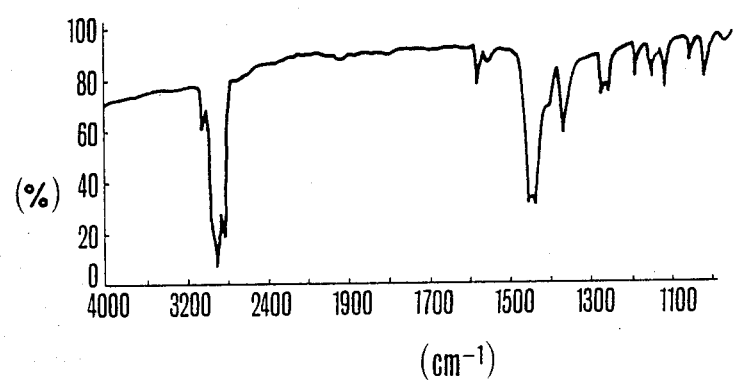
FIG. 1 is a diagrammatic representation of an infrared absorption spectrum of bis[tri(ortho-tolyl)phosphine] palladium according to the Nujol method using an NaCl plate casting.

The palladium complex provided according to this invention is a yellow crystalline powder of bis[tri(ortho-tolyl)phosphine] palladium having the following general formula:

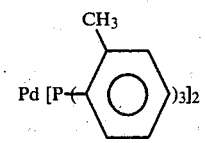

This complex decomposes at a temperature of higher than 200° C. in air and is also extremely stable, not showing any change after having been left in air for a long period of time. For the purpose of comparison, the decomposition temperature, color and stability of the known zero-valence palladium-phosphine complexes and the complex of this invention are shown in Table 1 below.

such as π-arylpalladium chloride. One may first prepare a zero-valent palladium compound such as bis-π-arylpalladium or π-arylcyclopentanedienylpalladium and then react this product with tri(ortho-tolyl)phosphine to form a zero-valent palladium-phosphine complex.

TABLE 1

| | No. | Pd (0) phosphine | Color | Decomposition point (°C.) | Stability (when left in the air) |
|---|---|---|---|---|---|
| This invention | 1 | [(C$_6$H$_4$-CH$_3$)$_3$P]$_2$Pd | Yellow | 201–210 | No change in quality for period of more than half a year |
| Known compounds | 2 | (p-CH$_3$O . C$_6$H$_4$ . NC) . [p-Cl C$_6$H$_4$)$_3$P]$_3$Pd | Colorless | 90–100 | Discolored and degenerated in a few days |
| | 3 | [(C$_6$H$_5$)$_3$P]$_4$Pd | Yellow | 100–105 | Discolored and degenerated in a few days |
| | 4 | [(p-Cl . C$_6$H$_4$)$_3$P]$_4$Pd | Orange | 120–160 | Discolored and degenerated in a few days |
| | 5 | [(p-Cl . C$_6$H$_4$)$_3$P]$_3$Pd | Yellow | 90–100 | Discolored and degenerated in a few days |
| | 6 | [(p-CH$_3$ C$_6$H$_4$)$_3$P]$_3$Pd | Golden yellow | 110 | Discolored and degenerated in a few days |
| | 7 | [(C$_6$H$_4$-CH$_3$)$_3$P]$_2$Pd—(dimethyl maleate complex: H(COOCH$_3$)C=C(COOCH$_3$)H) | Yellow | 174–176 | Discolored and degenerated in a few days |
| | 8 | [(C$_6$H$_4$-CH$_3$)$_3$P]$_2$Pd—(maleic anhydride complex) | Yellow | 180–213 | Discolored and degenerated in a few days |
| | 9 | [(C$_6$H$_4$-CH$_3$)$_3$P]$_2$Pd—(benzoquinone complex) | Dark red | 217–218 | Discolored and degenerated in a few days |
| | 10 | [(C$_6$H$_4$-CH$_3$)$_3$P]$_2$Pd—(naphthoquinone complex) | Reddish orange | 220–224 | Discolored and degenerated in a few days |

The zero-valent palladium-phosphine complex according to this invention can be produced by reacting a divalent or monovalent palladium salt with an organic phosphine and then reducing the reaction product. The reducing agent used for such reduction may be NH$_2$.NH$_2$, an alkali metal or an alkali metal salt. The alkali metal salts usable as the reducing agent for the reduction include alkali hydroxides such as NaOH, KOH, etc., alkali metal alkoxides such as NaOR, KOR (R: an alkyl or phenyl group), etc., and alkali metal carbonates such as Na$_2$CO$_3$, K$_2$CO$_3$, etc. The palladium salts usable in the reaction of this invention include inorganic salts such as PdCl$_2$, PdBr$_2$, Pd(NO$_3$)$_2$, etc., organic salts such as Pd(OCOCH$_3$)$_2$, Pd(OCOCH$_2$CH$_3$)$_2$, etc., and monovalent palladium salts According to this invention, the object palladium complex is obtained by reacting a palladium salt (PdX$_2$) with tri(ortho-tolyl)phosphine (L) to form PdL$_2$X$_2$ and then reducing the latter into bis[tri(ortho-tolyl)phosphine] palladium, (PdL$_2$), by using PdL$_2$X$_2$ which is free of PdX$_2$ and an alcoholic alkali (an alcoholic solution of an alkali metal hydroxide) as a reducing agent. The reason for the preference for the stated reducing agent is that when a strong reducing agent such as NH$_2$.NH$_2$ or an alkali metal is used and/or PdX$_2$ is mixed therein, palladium metal is liable to be by-produced. More specifically in the present invention, after dissolving a palladium salt in an acid, tri(ortho-tolyl)- phosphine is added thereto in an amount of 2 to 5 times the molar quantity of the palladium salt, and then after further adding thereto an alcohol, the mixture is refluxed for 0.5 to 10 hours to form a bis[tri(ortho-tolyl)-phosphine] palladium salt, $(PdL_2X_2)$. It is also recommended to add a solution of tri(ortho-tolyl)phosphine in toluene to an aqueous solution of a palladium salt and react them while maintaining the two separate phases to obtain $PdL_2X_2$. $PdL_2X_2$ separated from the reaction solution is added into an organic solvent together with tri(ortho-tolyl)phosphine (L) and reacted at a temperature lower than 150° C. in the presence of an alcoholic alkali hydroxide, and the resultant reaction product is separated, washed and then dried, whereby bis[tri(ortho-tolyl)phosphine] palladium, $(PdL_2)$, in the form of crystalline powder is obtained in a high yield.

The palladium complex of this invention is useful as a catalyst for organic syntheses and finds its best application as a catalyst for the oligomerization of 1,3-dienes. 1,3-dienes contemplated here are expressed by the general structural formula:

$$CH_2=C-C=CH_2$$
$$\phantom{CH_2=}R_1\phantom{-C=}R_2$$

(where $R_1$ and $R_2$ are each hydrogen or an alkyl group), and typical examples thereof are butadiene and isoprene.

Dimerization of a 1,3-diene gives a dimer, or in the presence of a nucleophilic reagent gives a compound composed of the dimer of 1,3-diene, to which the nucleophilic reagent is added. The nucleophilic reagent used in this reaction may be, for example, water, an alcohol, a carboxylic acid, an active methylene compound, ammonia, an aldehyde, an amine, acetic acid, phenol, formic acid or the like. The molar ratio of the palladium complex to 1,3-diene used in this reaction is usually within the range of 1 to $10^{-6}$, preferably $10^{-1}$ to $10^{-5}$. The reaction temperature may be selected from within the range of $-30°$ to $150°$ C., preferably $0°$ to $100°$ C., and the reaction time is usually less than 48 hours, preferably less than 20 hours. A longer time of reaction tends to increase the amount of the high-boiling by-product.

The palladium complex according to this invention, as appreciated from the Examples shown later, is stronger in activity and better in selectivity than the conventional catalysts. Such palladium complex is also characterized by its peculiar solubility in comparison with the conventional complexes. That is, the conventional complexes are easily soluble in the ordinary organic compounds, whereas the complex of this invention, although easily soluble in 1,3-dienes, is rather sparingly soluble in the ordinary organic compounds. Therefore, when a dimerization of a 1,3-diene is carried out by using the complex of this invention for producing the 1,3-diene dimer, the reaction proceeds in a homogenous system, but when the product, after the reaction, is distilled at a temperature of lower than 150° C., bis[tri(ortho-tolyl)phosphine] palladium is precipitated in the form of solid. Therefore, the catalyst can be separated while maintaining its activity and can be immediately put to reuse. The conventional complex catalysts are dissolved uniformly in the distillation residue, so that recovery thereof required complicated processing and also reactivation of the recovered catalyst was necessary. The complex of this invention has technically advantageous characteristics in these points.

A 1,3-diene is subjected to a dimerization by using the complex of this invention under predetermined conditions and the reaction product as well as the unreacted materials are distilled out at a temperature of less than 150° C. and, if necessary, under reduced pressure. The compound $PdL_2$ precipitated in the residual solution is separated by means of filtration or centrifugation. If desired, before condensation or separation, it may be diluted with a saturated hydrocarbon such as pentane, hexane, petroleum ether, etc., to facilitate separation. The separated complex of this invention can be immediately put to reuse. This is a prominent economical advantage over the conventional complexes.

The 1,3-diene oligomers have an extremely high reactivity, so that they can be applied for diversified purposes, for example in the field of synthetic drying oils or as intermediates for industrial production of chemical substances such as paints, high-molecular materials, etc., and as intermediates for the preparation of drugs and medicines.

The invention is now described in further detail by way of some examples.

EXAMPLE 1

Into a 1-l round flask 10.65 g (0.06 mole) of palladium chloride, 300 ml of water and 30 ml of concentrated hydrochloric acid were introduced, and after dissolving the solid material uniformly with agitation, 36.5 g (0.12 mole) of tri(ortho-tolyl)phosphine were added to the mixed solution, and after further introducing 300 ml of ethanol, the mixed solution was refluxed under heating for 2.5 hours. After cooling, the reaction mixture was filtered and the filtrate was washed with ethanol and then dried, obtaining 41.2 g of yellow bis[tri(ortho-tolyl)phosphine] palladium chloride,

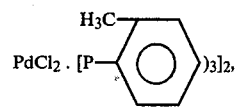

(decomposition temperature: 272°–278° C.) in a yield of 99.9%.

Figure 2:
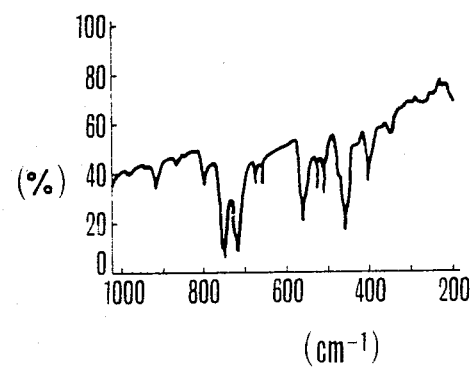
FIG. 2 is a similar representation as determined according to the Nujol method using a polyethylene casting.

39.5 g (0.05 mole) of this bis[tri(ortho-tolyl)phosphine] palladium chloride, 15.2 g (0.05 mole) of tri(ortho-tolyl)phosphine and 200 ml of toluene were put into a flask and agitated, and then 100 ml of ethanolic solution of 4.2 g of of sodium hydroxide was added and the mixture was heated at an external temperature of 120° C. for 5.5 hours. After cooling down naturally, a crystalline substance separated from the reaction solution. The substance was then dried to obtain 36.0 g of yellow solid crystalline powder. When hydrazine was used instead of sodium hydroxide as a reducing agent a large quantity of black palladium metal was precipitated during the reaction. When triethylamine was used as a reducing agent, almost no object substance was obtained. The obtained yellow powder was identified as bis[tri(ortho-tolyl)phosphine] palladium by the results of elemental analysis, infrared absorption spectroscopy (FIGS. 1 and 2) and determinations of molecular weight and NMR. In FIGS. 1 and 2, percent transmission is plotted as the ordinate and the wave number (cm$^{-1}$) as the abscissa.

Properties of bis[tri(ortho-tolyl)phosphine] palladium (1) Melting point: 201°–210° C. (decomposed)
(2) Molecular weight as measured according to vapour pressure osmotics method: 710 (theoretical: 715.2)
(3) Elemental analysis:
   Found (%): Pd*; 15.13; C, 70.13; H, 5.80.
   Calculated (%): Pd, 14.88; C, 70.53; H, 5.92.

*Determination of Pd: 1.9333 g of sample was treated with carbon monoxide in n-nonane and then heated to 150° C. to precipitate black palladium, and then the latter was filtered and separated and then further treated with a mixture of nitric acid and acetic acid to obtain 0.6172 g of palladium acetate (0.2926 g when reduced to the Pd basis).

EXAMPLE 2

Into a 300-ml three necked flask 100 ml (1 mole) of isoprene and 0.715 g (1 mmole) of bis[tri(ortho-tolyl)phosphine] palladium were introduced, and after further adding 80 ml (2 moles) of methanol in a nitrogen atmosphere, the mixture was reacted with agitation at 35° C. for 6 hours. The resultant reaction product was analyzed by gas chromatography to determine the yield of the entire reaction product and the proportion (percentage) of the respective individual products, the results being shown as Run No. 1 in Table 2 below.

The individual products I, II, III, IV and V were identified as follows by NMR, IR and mass spectral analysis.

Product I: Isoprene dimer (a substance having a triene structure)
Product II: 1-methoxy-2,6-dimethyl-2,7-octadiene

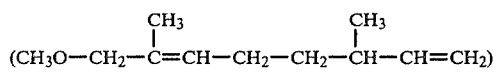

Product III: Isomer of product II
Product IV: Isoprene trimer
Product V: Isoprene tetramer For the purpose of comparison, the above reaction repeated using the following catalyst systems instead of bis[tri(ortho-tolyl)phosphine] palladium under the same conditions as Run No. 1.

Run No. 2: Palladium acetate (1 mmole) and ortho-tolylphosphine (2 mmoles)
Run No. 3: Palladium chloride (1 mmole), ortho-tolylphosphine (2 mmoles) and NaOCH₃ (3 mmoles)
Run No. 4: Palladium acetate (1 mmole) and triphenylphosphine (2 mmoles)
Run No. 5: Palladium chloride (1 mmole), triphenylphosphine (2 mmoles) and NaOCH₃ (3 mmoles)
Run No. 6: Palladium acetate (1 mmole), triphenylphosphine (2 mmoles) and NaOCH₃ (3 mmoles)
Run No. 7: Tetrakis(triphenylphosphine) palladium (1 mmole)

Similar reactions were also conducted in a 500-ml autoclave at a reaction temperature of 60° C., and the results are shown as Run No. 8 (this invention) and Run Nos. 9–14 (comparative examples) in Table 2.

When using the conventional catalysts, the yield of product was low at both reaction temperatures of 35° C. and 60° C. In Run Nos. 3, 4, 5, 6, 10, 11, 12 and 13 where divalent palladium was used as the catalyst, precipitation of palladium metal was observed during the reaction. Selectivity of 1-methoxy-2,6-dimethyl-2,7-octadiene (II) is improved as the reaction temperature is lowered. The results of Table 2 indicate that bis[tri(ortho-tolyl)phosphine] palladium has a high activity even at low temperatures, is capable of providing a high yield of the product and also has an excellent selectivity.

TABLE 2

| Run No. | | Catalyst | Reaction temp. (°C.) | Yield (g) | Proportion (%) of individual products | | | | |
|---|---|---|---|---|---|---|---|---|---|
| | | | | | I | II | III | IV | V |
| This invention | 1 | CH₃ Pd[P-(◯)₃]₂ | 35 | 85.2 | 10.2 | 67.2 | 19.2 | 0.4 | 3.0 |
| Known compounds | 2 | Pd(OCOCH₃)₂ and P-(◯)₃ H₃C | " | 0.0 | — | — | — | — | — |
| | 3 | PdCl₂, P-(◯)₃ and NaOCH₃ CH₃ | " | 42.0 | 11.6 | 66.5 | 20.7 | 0.5 | 0.7 |
| | 4 | Pd(OCOCH₃)₂ and P-(◯)₃ | " | 0.0 | — | — | — | — | — |
| | 5 | PdCl₂, P-(◯)₃ and NaOCH₃ | " | 45.1 | 9.0 | 60.0 | 18.8 | 11.0 | 1.2 |
| | 6 | Pd(OCOCH₃)₂, P-(◯)₃ and NaOCH₃ | " | 45.6 | 11.3 | 57.6 | 19.8 | 10.3 | 1.0 |
| | 7 | Pd[P-(◯)₃]₄ | " | 2.4 | 11.5 | 60.5 | 26.5 | 0.4 | 1.1 |
| This invention | 8 | CH₃ Pd[P-(◯)₃]₂ | 60 | 87.7 | 24.2 | 54.0 | 18.3 | 1.7 | 1.0 |
| Known compounds | 9 | Same as No. 2 | " | 1.3 | 31.9 | 53.0 | 10.4 | 1.4 | 3.3 |
| | 10 | Same as No. 3 | " | 42.6 | 24.6 | 54.3 | 18.6 | 2.3 | 0.2 |
| | 11 | Same as No. 4 | " | 1.0 | 42.3 | 42.8 | 10.0 | 4.9 | 0.0 |
| | 12 | Same as No. 5 | " | 44.3 | 15.4 | 39.8 | 28.4 | 14.0 | 2.4 |
| | 13 | Same as No. 6 | " | 42.0 | 20.7 | 37.0 | 27.9 | 12.3 | 2.1 |

TABLE 2-continued

| Run No. | Catalyst | Reaction temp. (°C.) | Yield (g) | Proportion (%) of individual products | | | | |
|---|---|---|---|---|---|---|---|---|
| | | | | I | II | III | IV | V |
| 14 | Same as No. 7 | " | 3.5 | 19.1 | 34.5 | 45.2 | 0.7 | 0.5 |

Reaction conditions: 100 ml (1 mole) of isoprene, 80 ml (2 moles) of CH₃OH; reaction time: 6 hours.

EXAMPLE 3

To the reaction product obtained in Run No. 1 of Example 2 0.06 g (0.2 mmole) of tri(ortho-tolyl)phosphine was added and the product was distilled out at an external temperature of 70° C. under a reduced pressure of 3 mmHg, thereby obtaining 3 g of evaporation residue containing a yellow precipitate. After adding hexane, the yellow precipitate was filtered, washed and then dried to obtain 0.70 g of yellow solids. The recovered yellow solid was identified as bis[tri(ortho-tolyl)phosphine] palladium as a result of similar analyses as in Example 1. Then an isoprene-methanol reaction was conducted under the same conditions as Example 2 (Run No. 1) by using 3.50 g of said recovered substance. The yield and the proportion of 1-methoxy-2,6-dimethyl-2,7-octadiene in the product were 86.0 g and 69.2%, respectively.

EXAMPLE 4

Into a 1-l autoclave 445.5 g (8.24 moles) of butadiene and 5.89 g (8.24 mmoles) of bis[tri(ortho-tolyl)phosphine] palladium were introduced, and after raising the temperature of the introduced mixture to 40° C. under agitation, 181.4 g (4.12 moles) of acetaldeyde were added and the mixture was reacted for 7.5 hours. After the reaction was over, unreacted materials were removed and the yield of the whole reaction product and the selectivity (percentage) of the individual products were determined by a determination of weight of the reaction product and an analysis by gas chromatography. The results are shown as Run No. 15 in Table 3 below.

The individual products were identified as follows as a result of said analysis.
Product A: 1,3,7-octatriene
Product B: 2,5-divinyl-6-methyl-tetrahydropyran
Product C: 1-methyl-2-vinyl-4,6-heptadienol
Product D: 1-methyl-2-vinyl-4,6-heptadieneyl acetate
Product E: High-boiling material Run Nos. 16–19 show the results of similar reactions conducted by using the known catalyst systems instead of bis[tri(ortho-tolyl)phosphine] palladium of Run No. 15 for the sake of comparison.

TABLE 3

| Run No. | | Catalyst | Reaction product yield (g) | Selectivity (%) | | | | |
|---|---|---|---|---|---|---|---|---|
| | | | | A | B | C | D | E |
| This invention | 15 | 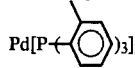 | 8.24 mmol | 576.5 | 1.0 | 2.0 | 89.9 | 2.1 | 5.0 |
| Known compounds | 16 | Pd(OCOCH₃)₂ 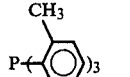 | 8.24 mmol plus 16.48 mmol | 322.5 | 5.8 | 2.3 | 61.0 | 6.5 | 24.4 |
| | 17 | Pd(OCOCH₃)₂ 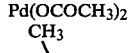 | 8.24 mmol plus 49.44 mmol | 319.7 | 8.2 | 3.8 | 61.5 | 5.0 | 21.5 |
| | 18 | Pd(OAc)₂ 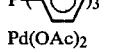 | 8.24 mmol plus 16.48 mmol | 329.3 | 0.4 | 37.1 o | 51.8 | 0.2 | 10.5 |
| | 19 |  | 8.24 mmol | 40.7 | 24.7 | 66.2 | 0.2 | 0.1 | 8.8 |

Reaction conditions: 8.24 moles of butadiene, 4.12 moles of acetaldehyde;
Pd concentration: 8.24 mmol; 40° C., 7.5 hr.

As apparent from Table 3 above, bis[tri(ortho-tolyl)phosphine] palladium gives a higher yield of product than other known catalysts and also has high selectivity for producing 1-methyl-2-vinyl-4,6-heptadienol. Thus, the catalyst of this invention is active at low temperatures and also high in selectivity without requiring any organic solvent such as employed in the conventional methods.

EXAMPLE 5

After distilling out, under a reduced pressure of 1 mmHg, the product mainly composed of 1-methyl-2-vinyl-4,6-heptadienol from 576 g of the reaction product in Run No. 15 of Example 4 at an external temperature of 100°–110° C., 51.5 g of the high-boiling residual liquid containing the catalytic precipitate was diluted with hexane and then filtered to obtain 4.12 g of bis[tri(ortho-tolyl)phosphine] palladium.

Then a reaction was carried out by using the recovered bis[tri(ortho-tolyl)phosphine] palladium as in Run No. 15 of Example 4, obtaining the results shown as Run No. 20 in Table 4 below. Both yield and selectivity were much the same as those in Run No. 15.

TABLE 4

| No. | Catalyst | Reaction product yield(g) | Selectivity (%) | | | | | Remarks |
|---|---|---|---|---|---|---|---|---|
| | | | A | B | C | D | E | |
| 15 | 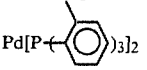 | 576.5 | 1.0 | 2.0 | 89.9 | 2.1 | 5.0 | Fresh catalyst |
| 20 | " | 576.3 | 1.1 | 2.1 | 89.6 | 2.1 | 5.1 | Recovered catalyst |

What is claimed is:

1. In the method for producing a hydroxy containing 1,3-diene oligomer by reacting a 1,3-diene of the formula of $CH_2=CR^1-CR^2=CH_2$, wherein $R^1$ and $R^2$ are identical or different and are hydrogen or alkyl, with an aldehyde, the improvement comprising using, as a catalyst, bis[tri(ortho-tolyl)phosphine] palladium having the formula

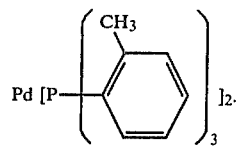

2. The method of claim 1, wherein said bis[tri(ortho-tolyl)phosphine] palladium catalyst is separated from the product and is immediately reused.

* * * * *